US006455710B1

(12) United States Patent
Villa et al.

(10) Patent No.: US 6,455,710 B1
(45) Date of Patent: Sep. 24, 2002

(54) METHOD FOR THE PREPARATION OF PURE CITALOPRAM

(75) Inventors: Marco Villa, Padova (IT); Federico Sbrogiò, Favaro Veneto (IT); Robert Dancer, Frederiksberg (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/046,126

(22) Filed: Jan. 8, 2002

Related U.S. Application Data

(63) Continuation of application No. PCT/DK01/00147, filed on Mar. 7, 2001.

(30) Foreign Application Priority Data

Dec. 22, 2000 (DK) .......................................... 2000 01929

(51) Int. Cl.[7] ............................................. C01D 307/87
(52) U.S. Cl. ...................................................... 549/462
(58) Field of Search ........................................ 549/462

(56) References Cited

U.S. PATENT DOCUMENTS

| | | | |
|---|---|---|---|
| 3,467,675 A | 9/1969 | Petersen et al. .......... | 260/346.2 |
| 4,136,193 A | 1/1979 | Bogeso et al. ............... | 424/285 |
| 4,650,884 A | 3/1987 | Bogeso ........................ | 549/467 |
| 4,943,591 A | 6/1990 | Boegesoe et al. ........... | 415/469 |
| 5,296,507 A | 3/1994 | Tanaka et al. ............... | 514/465 |
| 6,020,501 A | 2/2000 | Massonne et al. ........... | 549/307 |
| 6,028,204 A | 2/2000 | Massonne et al. ........... | 549/307 |
| 6,229,026 B1 | 5/2001 | Petersen ...................... | 549/467 |
| 6,258,842 B1 | 7/2001 | Petersen et al. ............. | 514/469 |
| 6,291,689 B1 | 9/2001 | Petersen et al. ............. | 549/467 |
| 6,365,747 B1 | 4/2002 | Dall'Asta et al. ............ | 548/146 |
| 2001/0027256 A1 | 10/2001 | Petersen et al. ............. | 549/462 |
| 2002/0004604 A1 | 1/2002 | Petersen et al. ............. | 549/462 |
| 2002/0019546 A1 | 2/2002 | Petersen et al. ............. | 549/307 |
| 2002/0025982 A1 | 2/2002 | Petersen et al. ............. | 514/469 |
| 2002/0026062 A1 | 2/2002 | Petersen et al. ............. | 549/467 |
| 2002/0028956 A1 | 3/2002 | Weber ......................... | 549/307 |
| 2002/0035277 A1 | 3/2002 | Rock et al. .................. | 549/467 |
| 2002/0040153 A1 | 4/2002 | Petersen ...................... | 549/467 |

FOREIGN PATENT DOCUMENTS

| | | | |
|---|---|---|---|
| CA | 2 023 057 | 2/1991 | ......... C07C/209/84 |
| EP | 0 413 259 A2 | 2/1991 | ......... C07C/209/82 |
| EP | 1 095 926 | 5/2001 | ........... C07C/33/46 |
| WO | 98/19511 | 5/1998 | |
| WO | 98/19512 | 5/1998 | |
| WO | 98/19513 | 5/1998 | |
| WO | 99/30548 | 6/1999 | |
| WO | 00/11926 | 3/2000 | |
| WO | 00/12044 | 3/2000 | |
| WO | 00/13648 | 3/2000 | |
| WO | 00/23431 | 4/2000 | ......... C07D/307/87 |
| WO | 00/39112 | 7/2000 | ......... C07D/307/87 |
| WO | 00/44738 | 8/2000 | ......... C07D/307/88 |
| WO | 01/47877 | 7/2001 | |
| WO | 01/66536 | 9/2001 | ......... C07D/307/87 |

OTHER PUBLICATIONS

Levy, L.F., "4–Aminophthalide and Some Derivatives", *J. Chem. Soc.* pp. 867–870 (1931).

Tirouflet J., "Phtalide Substitutes en 5", *Bull. Soc. Sci. de Bretagne* 26:35–43 (1951).

Bigler, Allan et al., "Quantitative Structure–activity Relationships in a Series of Selective 5–HT uptake inhibitors," *Eur. J. Med. Chem.* 3:289–295 (1997).

Forney L., "Reaction of Terephthalic Acid with Formaldehyde in Sulfur Trioxide Media," *J. Org. Chem.* 35:1695–1696 (1970).

Dordor et al., "Reaction of Oxazolines with Phosphorus Oxychloride," *Tetrahedron Letters* 24:1437–1440 (1993).

Barton et al., *Comprehensive Organic Chemistry*. The Synthesis and Reactions of Organic Compounds, vol. 2, pp. 1024–1025.

*Primary Examiner*—Amelia Owens
(74) *Attorney, Agent, or Firm*—Darby & Darby

(57) ABSTRACT

The present invention relates to the process for the preparation and purification of citalopram (I)

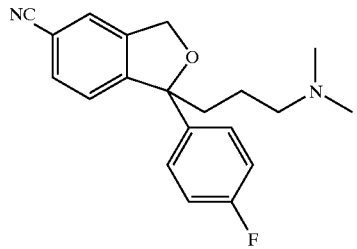

in which a compound of formula (II)

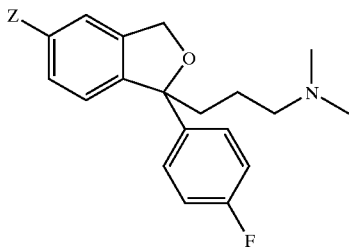

wherein Z is iodo, bromo, chloro or $CF_3-(CF_2)_n-SO_2-O-$, n being 0, 1, 2, 3, 4, 5, 6, 7 or 8, is subjected to a cyanide exchange reaction with a cyanide source; the resultant crude citalopram product is optionally subjected to some initial purification and subsequently treated with an amide or an amide-like group forming agent; the reaction mixture is then subjected to an acid/base wash and/or crystallisation and recrystallisation of citalopram in order to remove the amides formed from the crude citalopram mixture; and the resulting citalopram product is optionally further purified, worked up and isolated as the base or a pharmaceutically acceptable salt thereof.

12 Claims, No Drawings

METHOD FOR THE PREPARATION OF PURE CITALOPRAM

This is a continuation of application No. PCT/DK01/00147, filed Mar. 7, 2001.

The present invention relates to a process for the manufacture of the well-known antidepressant drug citalopram, 1-[3-(dimethylamino)propyl]-1-(4fluorophenyl)-1,3-dihydro-5-isobenzofuran-carbonitrile, in particular a process for preparing pure citalopram by cyanide exchange.

BACKGROUND OF THE INVENTION

Citalopram is a well-known antidepressant drug that has now been on the market for some years and has the following structure:

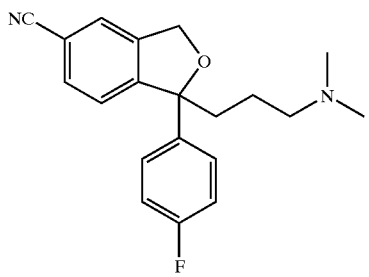

(I)

It is a selective, centrally acting serotonin (5-hydroxytryptamine; 5-HT) reuptake inhibitor, which has further been disclosed to show effects in the treatment of dementia and cerebrovascular disorders, cf. EP-A-474580.

Citalopram was fist disclosed in DE 2,657,013, corresponding to U.S. Pat. No. 4,136,193. This patent publication i.a. outlines a process for preparation of citalopram from the corresponding 5-bromo-derivative by reaction with cuprous cyanide in a suitable solvent. Further processes for the preparation of citalopram by exchange of 5-halogen or 5-CF'$_3$—(CF$_2$)$_n$—SO$_2$—O— with cyano are disclosed in WO 001 1926 and WO 0013648.

Other processes involve:
Conversion of a 5-amido or 5-ester group to a 5-cyano group (WO 9819513)
Conversion of a 5-amino group to a 5-cyano group (WO 9819512)
Conversion of a 5-formyl group to a 5-cyano group (WO 9900548)
Conversion of a 5-oxazolinyl or 5-thiazolinyl group to a 5-cyano group (WO 0023431)

It has turned out that it is difficult to manufacture citalopram in the required quality. The processes of DE 2,657,013, WO 0011926 and WO 0013648 comprising exchange of 5-halogen with cyano as described above have been found to give the desmethyl-citalopram derivative in unacceptable amounts. This impurity is difficult to remove by usual working up procedures leading to extensive and expensive purification processes.

Thus, a process for the removal of impurities formed during the preparation of citalopram by cyanide exchange reaction i.e. the exchange of 5-halogen or the like with 5-cyano, is necessary in order to obtain a commercially attractive manufacture of citalopram.

It has now been found that the desmethyl-citalopram impurity may be removed by reaction with an amide-forming group or a similar group. The amide formed may be separated from the final product by conventional work-up procedures.

SUMMARY OF THE INVENTION

Accordingly, the present invention provides a novel process for the preparation of citalopram of formula

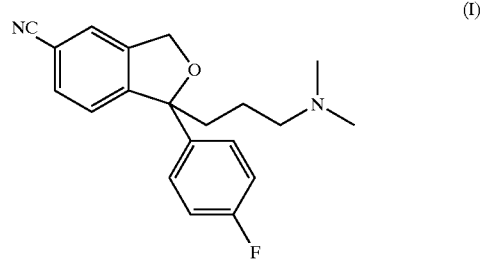

(I)

in which a compound of Formula II

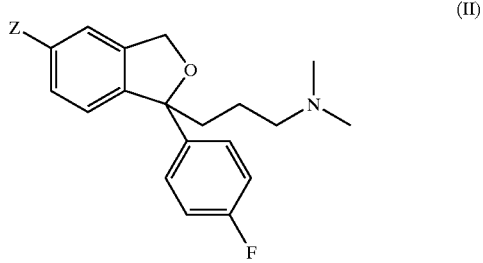

(II)

wherein Z is iodo, bromo, chloro or CF$_3$—(CF$_2$)$_n$—SO$_2$—O—, n being 0, 1, 2, 3, 4, 5, 6, 7 or 8, is subjected to a cyanide exchange reaction with a cyanide source; the resultant crude citalopram product is optionally subjected to some initial purification and subsequently treated with an amide or an amide-like group forming agent selected from the agents of formulas (a), (b) or (c):

R—CO—X  (a)

$$\underset{Hal}{\overset{Y}{\|}}{\underset{}{C}}{W—R''}$$  (b)

R'''—SO$_2$—Hal  (c)

where X is halogen or a group O—CO—R', Hal is halogen, Y is O or S, W is O, N or S and R, R', R" and R'" are each independently selected from the group consisting of hydrogen, alkyl optionally substituted aryl or aralkyl;
the reaction mixture is then subjected to an acid/base wash and/or crystallisation and recrystallisation of citalopram in order to remove the amides formed from the crude citalopram; and
the resulting citalopram product is optionally further purified, worked up and/or isolated as the base or as a pharmaceutically acceptable salt thereof.

In a further aspect, the invention relates to the above process in which the compound of formula II is the S-enantiomer and the product obtained is escitalopram.

In yet another aspect, the present invention relates to an antidepressant pharmaceutical composition comprising citalopram manufactured by the process of the invention.

According to the process of the invention, the desmethyl citalopram impurity of formula III

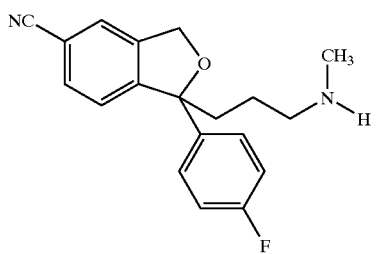

(III)

is reacted with the amide or amide-like group forming reagent of formula (a), (b) or (c) to form an amide or an amide-like compound of formula IV:

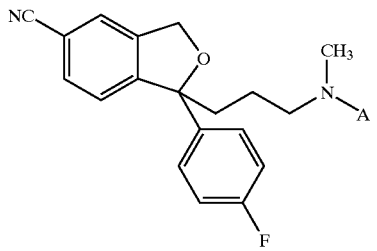

(IV)

wherein A is a group R—CO—, R'—CO—, R"—W—CY— or R'"—SO$_2$—, wherein R, R', R" and R'", W and Y are as defined above. The reaction product of formula IV may be removed by acid/base wash or crystallisation and discarded, and citalopram may be obtained as a pure product fulfilling the requirements of the health authorities. Furthermore, the reaction may be carried out under convenient conditions.

Throughout this specification with claims, halogen means chloro, bromo or iodo.

The term alkyl refers to a branched or unbranched alkyl group, such as methyl, ethyl, 1-propyl, 2-propyl, 1-butyl, 2-butyl, 2-methyl-2-propyl, and 2-methyl-1-propyl.

The term aryl refers to a carbocyclic aromatic group, such as phenyl. Aralkyl refers to a aryl-alkyl group wherein aryl and alkyl are as defined above. The aryl and aralkyl groups may optionally be substituted, e.g. with alkyl groups, forming for example tolyl.

The cyanide exchange reaction is a reaction where the substituent Z in the compound of formula II is exchanged with a cyano group. The cyanide exchange reaction may be carried out:

When Z is Br, by reaction with cuprous cyanide in a suitable solvent as described in U.S. Pat. No. 4,136,193, When Z is iodo, bromo, chloro or CF$_3$—(CF$_2$)$_n$—SO$_2$—O—, n being 0, 1, 2, 3, 4, 5, 6, 7 or 8, by reaction with a cyanide source in the presence of a palladium catalyst and a catalytic amount of Cu$^+$ or Zn$^{2+}$ as described in WO 0013648. Preferred cyanide sources are KCN, NaCN or ((R$^a$)$_4$N)CN where (R$^a$)$_4$ indicates four groups which may be the same or different and are selected from hydrogen and straight chain or branched alkyl. Alternatively the reaction may be carried out with Zn(CN)$_2$ in the presence of a palladium catalyst. The palladium catalyst may be any suitable Pd(0) or Pd(II) containing catalyst, such as Pd(PPh$_3$)$_4$, Pd$_2$(dba)$_3$, Pd(PPh$_3$)$_2$Cl$_2$, etc. The catalysts, the reaction conditions, Cu$^+$ and Zn$^{++}$ sources, etc are further described in WO 0013648.

The palladium catalysed process is in particular convenient when Z is Br.

When Z is Cl or Br, with a with a cyanide source in the presence of a nickel catalyst, as described in WO 0011926. Preferred cyanide sources are KCN, NaCN or ((R$^a$)$_4$N)CN where (R$^a$)$_4$ indicates four groups which may be the same or different and are selected from hydrogen and straight chain or branched alkyl. The reaction may optionally be carried out in the presence of a catalytic amount of Cu$^+$ or Zn$_{2+}$.

The nickel catalyst may be any suitable Ni(0) or Ni(II) containing complex which acts as a catalyst, such as Ni(PPh$_3$)$_3$, (σ-aryl)-Ni(PPh$_3$)$_2$Cl, etc and it is preferably prepared in situ. The nickel catalysts and the reaction conditions are further described in WO 0011926.

The nickel catalysed process is in particular convenient when Z is Cl.

The intermediate of formula II wherein Z is bromo or chloro may be prepared from bromo- and chlorophthalide, respectively, as described in DE 2,657,013. The compound wherein Z is iodo or Z is CF$_3$—(CF$_2$)$_n$—SO$_2$—O— may be prepared as described in WO 0013648. Preferably the intermediate wherein Z is Br is used.

The amide or amide-like group forming agent used in the process of the invention is preferably a compound of Formula (a), more preferably an acid anhydride or an acid halogenide, most preferably acetic anhydride or acetyl chloride. This agent is used in an amount of up to 10 mol/mol % of the amount of citalopram dependent on the content of the desmethyl-impurity of formula III.

The crude citalopram product resulting from the cyanide exchange reaction may be subjected to some initial purification before the citalopram product is reacted with an amide or an amide-like group forming agent, e.g. extraction, crystallisation, washing with a mixture of an aqueous and an organic solvent in order to remove metal salts.

The acid/base wash may be performed by:

Dissolving the crude citalopram product comprising the amide or amide like product of formula IV in a proper solvent, e.g. toluene, then adding an aqueous acid until the mixture is acidic (e.g. until pH is about 0.5–3, more preferably about 1) and separating the aqueous phase containing citalopram, discarding the organic phase comprising the amide or amide-like product of formula IV, and then making the aqueous phase basic by addition of a base, and dissolving the mixture in an organic solvent.

Then collecting the organic phase

The crude citalopram may be dissolved in any convenient solvent, preferably toluene.

The acid used may be any mineral acid, for example HCl, HBr, H$_2$SO$_4$ or H$_3$PO$_4$ or a carboxylic acid such as acetic acid, and the base used may be any convenient base, preferably NH$_3$ or NaOH. The second organic solvent may be any suitable solvent preferably the same as used in the first step of the acid/base wash.

Further removal of the amide or amide-like product of formula IV and other impurities may if necessary be carried out by crystallisation and/or recrystallisation of the citalopram base (cf. Dutch patent No 1016435) and/or crystallisation and re-crystallisation of a pharmaceutically acceptable salt of citalopram.

According to one preferred embodiment of the invention:

5-Bromo citalopram is reacted with a cyanide source as described above;

the resulting crude citalopram is isolated as the base in the form of an oil;

the reaction mixture is washed with a mixture of an aqueous solvent and an organic solvent, e.g.

a mixture of H$_2$O/ethylenediamine and toluene or of an aqueous EDTA-solution and toluene, in order to remove metal salt (originating from the cyanide source);

up to 10 mol/mol % acetic anhydride is added;

the reaction between the acetic anhydride and the desmethyl-citalopram impurity is allowed to take place, either neat or in a solvent;

the reaction mixture is acidified by addition of hydrochloric acid;

the aqueous phase containing the citalopram product is separated from the organic phase containing the acetamide impurity of formula IV (A=acetyl);

The organic phase is discarded;

The aqueous phase is made basic by addition of NH$_3$ or NaOH and an organic solvent is added;

The organic phase is collected and the free base is crystallised;

Thereafter, a pharmaceutically acceptable salt of citalopram, such as the hydrobromide or hydrochloride, may be prepared by methods known in the art.

Thus, the crystalline base may be reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously. The hydrobromide or hydrochloride of citalopram obtained by the method of the invention has a very high purity, preferably more than 99.7% pure, most preferably more than 99.8% purity. Other salts of citalopram, e.g. the oxalate, may also be obtained in a very pure form by this process.

The phamaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums and the like. Any other adjuvant or additive, colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Finally, it has been found that the base may be formulated into very good and stable solid formulations with good release properties (cf. Dutch patent No 1016435).

The invention is further illustrated by the following examples.

EXAMPLE 1

Preparation of Crude Citalopram Base (1-[3-(dimethylamino)propyl]-1-(4-fluorophenyl)-1,3-dihydro-5-isobenezofurancarbonitrile)

Cu(I)CN (197 g, 2.2 mol) is added to a solution of 1-[3-(dimethylamino)propyl]-1-(4-fluorophenyl)-1,3-dihydro-5-bromo-isobenzofurane (720 g, 1.9 mol) in sulfolane (250 mL). After the reaction mixture has been heated to 150° C. for a period of 5 hours, sulfolane (500 mL) is added. The reaction mixture is cooled to 80° C. where ethylenediamine (aq, 50% w/v) is added. Toluene (2 L) is added and the phases are separated.

The organic phase is further washed with EDTA (aq, 500 mL, 5% w/v) and water (2×500 mL). The volatile materials from the organic phase are removed in vacuo. 540 g of crude Citalopram base is isolated as an oil. Purity approx. 85% by HPLC (Peak area)

EXAMPLE 2

Purification of Crude Citalopram by Removing 1-[3-(methylamino)propyl]-1-(4-fluorophenyl)-1,3-dihydro-5-isobenzofurancarbonitrile as its Acetamide Crude citalopram base from Example 1 (324 g, 1 mol) having a content of approx. 25% mol/mol of 1-[3-(methylamino)propyl]-1-(4-fluorophenyl)-1,3-dihydro-5-isobenzofurancarbonitrile is dissolved in toluene (1.5 L). Acetic anhydride (10 g, 0.1 mole) is added and the reaction mixture is heated to 60° C. for 30 min. Water (2 L) is added, the pH is adjusted to 1 by adding conc. HCl (aq, 12 M) and the phases are separated. The organic phase is discarded and the pH of the aqueous phase is adjusted to 9 with the addition of ammonia (aq, 25% w/v). Toluene (1.5 L) is added and phases are separated. The aqueous phase is discarded and the solvents are removed from the organic phase in vacuo. A yield of 330 g of an oil containing crude free base of citalopram and toluene is isolated. The content of 1-[3-(methylamino)propyl]-1-(4-fluorophenyl)-1,3-dihydro-5-isobenzofuran-carbonitrile is <0.1% mol/mol.

What is claimed is:

1. A process for the preparation of citalopram

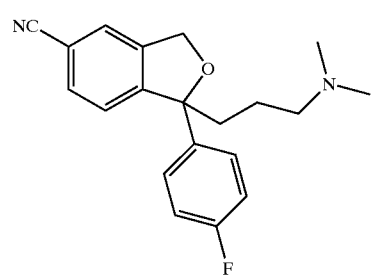

I in which a compound of formula II

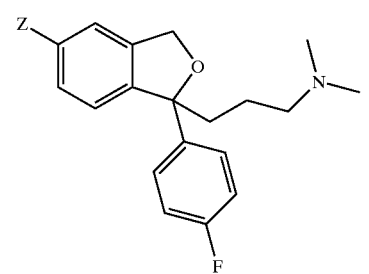

II wherein Z is iodo, bromo, chloro or CF$_3$—(CF$_2$)$_n$, —SO$_2$—O—, n being 0, 1, 2, 3, 4, 5, 6, 7 or 8, is subjected to a cyanide exchange reaction with a cyanide source; the resultant crude citalopram product is optionally purified and subsequently treated with an amide or an amide-like group forming agent selected from the compounds of Formulas (a), (b) or (c):

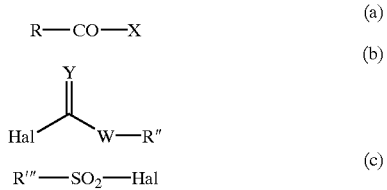

(a) R—CO—X (b)

(c) R'''—SO$_2$—Hal where X is halogen or a group O—CO—R', Hal is halogen, Y is O or S, W is O, N or S and R, R', R" and R'" are each selected from the group consisting of hydrogen, alkyl, and optionally substituted aryl or aralkyl;

the reaction mixture is then subjected to an acid/base wash or crystallisation and recrystallisation of citalopram in order to remove amides formed from the crude citalopram mixture; and the resulting citalopram product is optionally purified and isolated as the base or a pharmaceutically acceptable salt thereof.

2. The process of claim 1 wherein the amide or amide-like group forming agent is a compound of formula R—CO—X, wherein R and X are as defined in claim 1.

3. The process of claim 2 wherein the amide or amide-like group forming agent is a carboxylic acid anhydride or an acyl halogenide.

4. The process of claim 3 wherein the amide or amide-like group forming agent is acetic acid anhydride.

5. The process of claim 3 wherein the amide or amide-like group forming agent is an acylchloride.

6. The process of claim 5, wherein the acylchloride is acetylchloride.

7. The process of one of claims 1–5 wherein Z is Br and the cyanide reaction is carried out by reaction with cuprous cyanide in a solvent.

8. The process of one of claims 1–5 wherein Z is iodo, bromo, chloro or $CF_3$—$(CF_2)_n$—$SO_2$—O—, n being 0, 1, 2, 3, 4, 5, 6, 7 or 8, and the cyanide exchange reaction is carried out by reaction with a cyanide source in the presence of a palladium catalyst and a catalytic amount of $Cu^+$ or $Zn^{2+}$.

9. The process of one of claims 1–5 wherein Z is iodo, bromo, chloro or $CF_3$—$(CF_2)_n$—$SO_2$—O—, n being 0, 1, 2, 3, 4, 5, 6, 7 or 8, and the cyanide exchange reaction is carried out with $Zn(CN)_2$ in the presence of a palladium catalyst.

10. The process of claim 9 wherein Z is Br.

11. The process of one of claims 1–5 wherein Z is Cl or Br and the cyanide exchange reaction is carried out with a cyanide source in the presence of a nickel catalyst, optionally in the presence of a catalytic amount of $Cu^+$ or $Zn^{2+}$.

12. The process of claim 11 wherein Z is Cl.

* * * * *

UNITED STATES PATENT AND TRADEMARK OFFICE
CERTIFICATE OF CORRECTION

PATENT NO.     : 6,455,710 B1
DATED          : September 24, 2002
INVENTOR(S)    : Marco Villa, Federico Sbrogio and Robert Dancer It is certified that error appears in the above-identified patent and that said Letters Patent is hereby corrected as shown below:

Column 6,
Lines 65-66, delete "$CF_3\text{-}(CF_2)_{n'}\text{-}SO_2\text{-}O\text{-}$" and replace with
-- "$CF_3\text{-}(CF_2)_n\text{-}SO_2\text{-}O\text{-}$" --

Signed and Sealed this

Twenty-fourth Day of June, 2003

JAMES E. ROGAN
*Director of the United States Patent and Trademark Office*